United States Patent [19]

Goldstein

[11] Patent Number: 4,807,753
[45] Date of Patent: Feb. 28, 1989

[54] DISPENSER AND PACKAGING FOR BANDAGE STRIPS

[76] Inventor: Nancy H. Goldstein, 3829 Windom Pl., NW., Washington, D.C. 20016

[21] Appl. No.: 141,133

[22] Filed: Mar. 14, 1988

Related U.S. Application Data

[62] Division of Ser. No. 815,031, Dec. 31, 1985.

[51] Int. Cl.$^4$ .................. A61B 17/06; A61B 19/02
[52] U.S. Cl. .................. 206/390; 206/440; 206/441; 206/820
[58] Field of Search .............. 206/390, 440, 441, 820

[56] References Cited

U.S. PATENT DOCUMENTS

| | | | |
|---|---|---|---|
| 3,330,471 | 7/1967 | Timms | 206/390 |
| 3,674,614 | 7/1972 | Templeton | 206/390 |
| 4,060,168 | 11/1977 | Romagnoli | 206/390 |
| 4,298,158 | 11/1981 | Hoppe et al. | 206/390 |
| 4,394,904 | 7/1983 | Larimore | 206/390 |
| 4,658,962 | 4/1987 | Burns et al. | 206/390 |

Primary Examiner—Joseph Man-Fu Moy

[57] ABSTRACT

A dispenser containing a plurality of packaged rolls of bandage strips includes a case having upper section and a lower section which accommodates packaged rolls of bandage strips. The case has at least one slot for dispensing bandage strips and the bottom side of the case has a flat area which can be adhered to a flat support. Each packaged roll of bandage strips includes a series of bandage strips disposed in end-to-end relation with packaging material surrounding the bandage strips, transverse seals for maintaining strips sterilely separate from each other, lines of weakness in the packaging material, each located forward of a respective seal for aiding the separation of the packaging material and a corresponding bandage strip from the remainder of the roll while maintaining the bandage strips in the remainder of the roll in a sealed sterile condition.

3 Claims, 3 Drawing Sheets

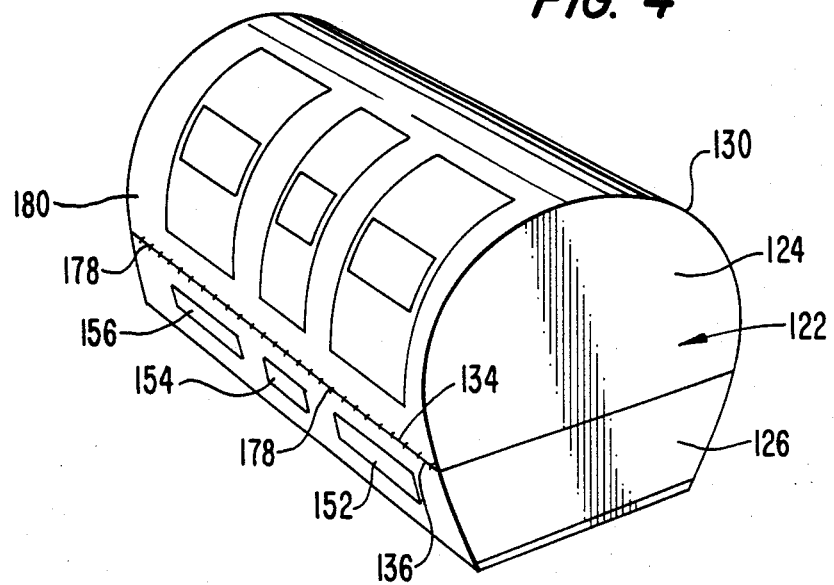
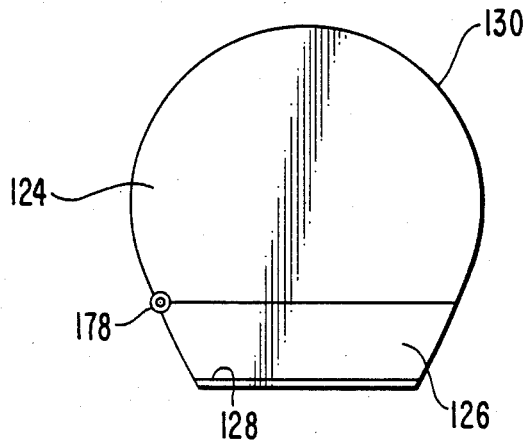
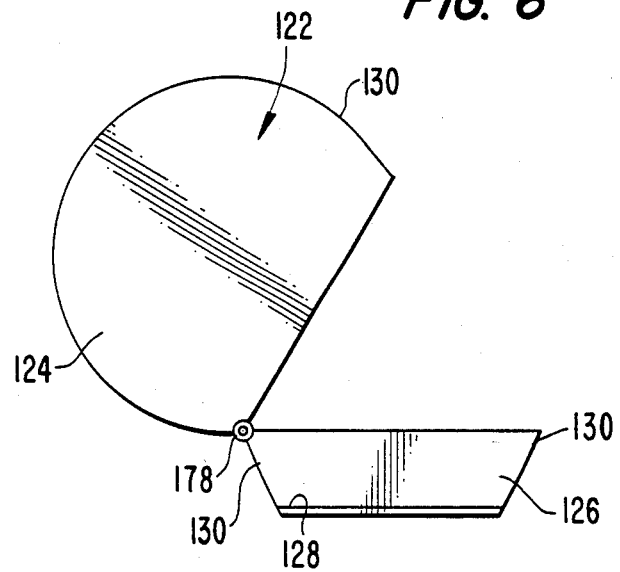

DISPENSER AND PACKAGING FOR BANDAGE STRIPS

This application is a division of application Ser. No. 815,031, filed Dec. 31, 1985.

BACKGROUND OF THE INVENTION

1. Field of the invention

The present invention relates to a dispenser and packaging for bandage strips.

2. Description of the related art

Bandage strips are well known first-aid devices which are used to cover contusions and abrasions. A conventional bandage strip includes a longitudinally running piece of adhesive tape with a central gauze portion. The gauze portion covers the contusion or abrasion and the adhesive portion holds the strip in place by adhering to adjacent areas of skin. The adhesive portion of the strip is usually covered by a backing paper which can be peeled away to expose the adhesive portion for use and prevent the adhesive portion from adhering to other surfaces prior to use.

Bandage strips are conventionally packaged in a sterile paper sleeve enclosure which is ripped open through the use of a pull-thread opening arrangement. The packaged bandage strips are conventionally stored in a rectangular container having a upper flap type lid which opens to reveal a mixed assortment of packaged bandage strips of various sizes and shapes.

The conventional manner of storing and packaging bandage strips has a number of drawbacks. The pull-thread opening arrangement for the packaging often fails, is hard to use, and is expensive to produce. Also, it is difficult to observe and select the desired bandage strip from the conventional container due to the tendency of its contents to become disorganized over time. There is a tendency to run out of the more popular types of bandage strips in the assortment thereby leaving an excess of the types of bandage strips which are used less often. these strips go to waste when another container of bandage strips is purchased. Also, conventional containers of bandage strips are easy to misplace and upset and require substantial headroom to open.

It is an object of the present invention to provide for an opening arrangement for the packaging of bandage strips which does not fail, is easy to use, and is inexpensive to produce.

It is also an object of the present invention to provide a manner of storing and packaging bandage strips which makes it easy to observe and select the desired bandage strip from the storage container.

It is another object of the present invention to provide a container for bandage strips which does not have a tendency to become disorganized over time.

It is a further object of the present invention to provide a manner of storing and packaging bandage strips so that an excess of the types of bandage strips which are used less often do not go to waste.

It is still a further object of the present invention to provide a container for bandage strips which is not easy to misplace or upset and which do not require substantial headroom to open.

It is an additional object of the present invention to provide a packaging arrangement for bandage strips which is easy to open while preserving sterility.

Additional objects and advantages of the invention will be set forth in the description that follows, and in part will be obvious from the description, or may be learned by practice of the invention. The objects and advantages of the invention may be realized and obtained by means of the intrumentalities and combinations particularly pointed out in the appended claims.

SUMMARY OF THE INVENTION

To achieve the foregoing objects, and in accordance with the purpose of the invention as embodied and broadly described herein, there is provided a dispenser for packaged rolls of bandage strips comprising: a case having an upper section, a lower section, a bottom side and an upper side; the upper and lower section each having two longitudinally running edges; the inside of the case having a plurality of areas, each for housing a roll of bandage strips; the case having a slot for dispensing bandage strips from separate rolls of bandage strips; the bottom side of the case having a flat area; and means attached to the flat area for adhering the flat area to a support.

It is preferable that the upper side of the case is generally rounded in cross section, that the dispenser includes hinge means for connecting one edge of the upper section to one edge of the lower section. In one embodiment it is preferable that the hinge means is positioned proximate to the bottom side of the case so that the upper section is pivotable away from the lower section to open the case for replacing a roll of bandage strips without requiring substantial headroom. In the second embodiment it is preferable that the slots are positioned proximate to the bottom side of the case and the hinge means is positioned high on the upper side so that the upper section is pivotable away from the lower section to open the case for replacing a roll of bandage strips without requiring substantial headroom and allowing ease in visability of the inside of the case.

In further accordance with the purposes of the present invention, there is provided packaged rolls of bandage strips comprising a series of bandage strips disposed in end-to-end relation; packaging material surrounding the bandage strips for maintaining the strips in the end-to-end relationship and in an sterile condition; transverse seal means in the packaging material for maintaining the strips sterilely separate from each other; and line of weakness means in the packaging material, each located forward of a respective seal means for aiding separation of the packaging material and a corresponding bandage strip from the remainder of the roll while maintaining the bandage strips in the remainder of the roll in a sealed sterile condition.

It is preferable that the length of a strip is greater than the distance between the seal means forward of the strip and the line of weakness behind the respective seal means so that the strip is easily removable from the packaging material after separation of the packaging material along the line of weakness means.

BRIEF DESCRIPTION OF THE DRAWINGS

The accompanying drawings, which are incorporated in and constitute a part of the specification, illustrate a preferred embodiment of the invention and, together with a general description given above and the detailed description of the preferred embodiment given below, serve to explain the principles of the invention.

FIG. 4 is a perspective view of a second embodiment of a dispenser incorporating the teachings of the present invention;

FIG. 5 is an end view of the embodiment shown in FIG. 4;

FIG. 6 is an end view of the embodiment shown in FIG. 4 in an open position;

DESCRIPTION OF THE PREFERRED EMBODIMENTS

Reference will now be made in detail to the present preferred embodiments of the invention as illustrated in the accompanying drawings.

Figure 1:
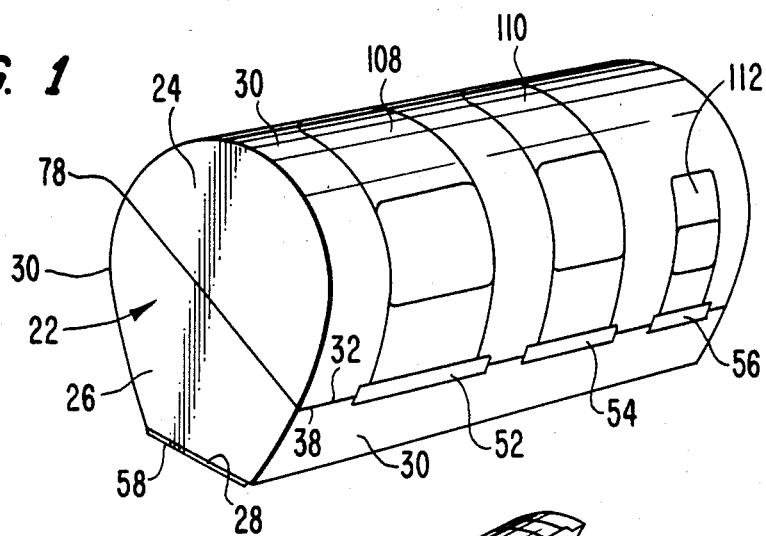
FIG. 1 is a perspective view of a dispenser for packaged rolls of bandage strips incorporating the teachings of the present invention.
Figure 2:
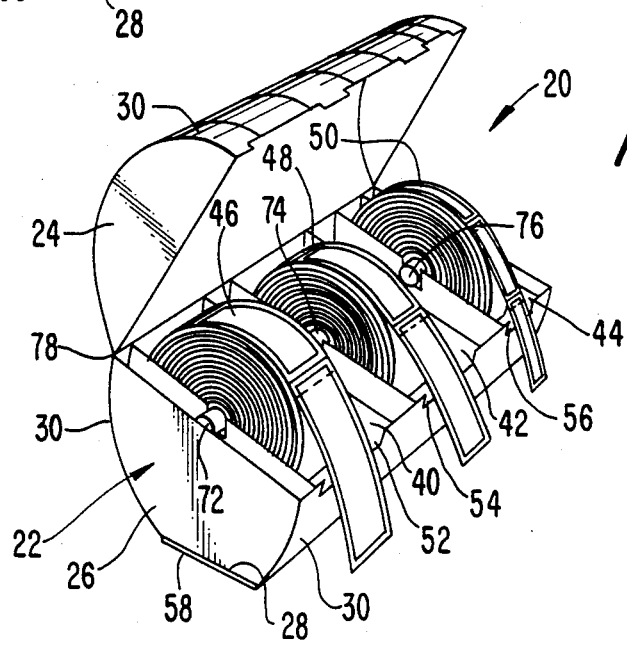
FIG. 2 is a perspective view of the dispenser illustrated in FIG. 1 in an open position and including packaged rolls of bandage strips incorporating the teachings of the present invention.
Figure 3:
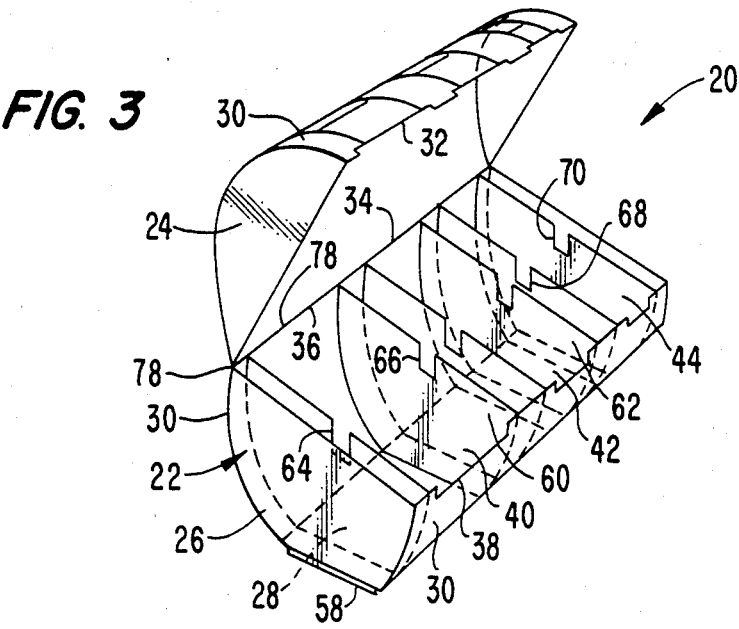
FIG. 3 is a perspective view of the dispenser shown in FIG. 2 without the rolls of bandage strips.

In accordance with the present invention there is provided a dispenser for packaged rolls of bandage strips comprising: a case having an upper section, a lower section, a bottom side and a upper side; the upper and lower sections each having two longitudinally running edges; the inside of the case having a plurality of areas, each for housing a roll of bandage strips; the case having slots for dispensing bandage strips from separate rolls of bandage strips; the bottom side of the case having a flat area; and means attached to the flat area for adhering the flat area to a support. As shown in FIGS. 1-3, dispenser 20 includes a case 22 which is molded or constructed from metal or plastic sheets. Case 22 includes an upper section 24 and a lower section 26 which are movable with respect to each other to allow access to the interior of case 22. Case 22 also includes a bottom side 28 constituting a flat area which is complementary to a flat support on which the dispenser can rest. The case also contains an upper side 30 which, as shown in FIGS. 1-3, includes the curved surfaces of upper section 24 and the curved surfaces on the lower section 26. Upper section 24 has two longitudinally running edges 32 and 34, and lower section 26 has longitudinally running edges 36 and 38, which are best shown in FIG. 3.

The inside of case 22 includes a plurality of areas 40, 42, and 44, each for housing a roll of bandage strips 46, 48 and 50 respectively. Case 22 also has slots 52, 54, and 56 for dispensing bandage strips. In FIGS. 1-3 it is seen that the sides of each of the slots 52, 54 and 56 are defined by edge 32 of upper section 24 and edge 38 of lower section 26. This arrangement precludes the need for threading the strips through a closed slot when replacing a roll of strips.

The bottom side of case 22 has a flat area and includes means attached to the flat area for adhering the flat area to a support. Such adhering means can comprise a strip of adhesive material 58 attached to the flat area of bottom side 28. The adhesive material 58 is covered with a removable paper which can be peeled away to expose the adhesive surface. The flat area of bottom side 28 can be adhered to a support such as a shelf in a medicine cabinet.

Upper side 30 of case 22 is generally rounded in cross section for accommodating the shape of the packaged roll of bandage strips 46, 48, 50. This allows the rolls of bandage strips to easily rotate in case 22 and is an economical use of space. Areas 40, 42, and 44 are separated by partitions 60 and 62 to further facilitate the rotation of the rolls of bandage strips. Slots 64, 66, 68 and 70 accommodate axles 72, 74 and 76 to additionally facilitate rotation of packaged bandage strips 46, 48 and 50. Hinge means such as hinge 78 is used for connecting one edge 34 of upper section 24 to one edge 36 of lower section 26.

Slots 52, 54 and 56 are of different widths so that each corresponds to a roll of bandage strips of a corresponding width. In such a manner, if bandage strips of a particular width are depleted before the other rolls are depleted, a replacement roll can be inserted without wasting the remaining strips in the other rolls. It is clearly contemplated that strips of differing shapes and lengths can be used as well as shapes of differing widths. As shown in FIG. 2, roll 46 is wider than roll 48 which is wider than roll 50. Slot 52 is wider than slot 54 which is wider than slot 56 in a corresponding fashion.

As shown in FIGS. 1 through 3, slots 52, 54 and 56, defined by edges 32 and 38, are positioned proximate to the bottom side 28 of the case, and hinge means such as hinge 78 is positioned high on the upper side 30 so that the upper section 24 is pivotable away from the lower section 26 to open the case 22 for replacing a roll of bandage strips without requiring substantial headroom and allowing ease in visibility of the inside of the case while doing so. In addition, this slanted positioning of the edges of the case in conjunction with the arrangement of slot 64, 66, 68 and 70 and axle 72, 74 and 76 caused the axles to be maintained in place in their respective slots.

The embodiment shown in FIGS. 4-6 allows the case 122 to be opened without requiring substantial headroom. Such an arrangement is especially important when the dispenser is attached to the shelf of a medicine cabinet having closely spaced shelves. Hinge means such as hinge 178 is used for connecting one edge 134 of upper section 124 to one edge 136 of lower section 126. Hinge 178 is positioned proximate to the bottom side 128 of the dispenser so that upper section 124 is pivotable away from lower section 126 to open case 122 as shown in FIG. 6 without requiring much head room. The general rounded upper side 130 contributes in this regard.

In the arrangement shown in FIGS. 4-6, case 122 has a front side 180 such that hinge 178 and slots 152, 154 and 156 are positioned on the front side of case 122 so that upper section 124 of case 122 is pivotable forward. When mounted on the shelf of a medicine cabinet, this allows upper section 124 to be pivoted forward, down, and past the front edge of the shelf to facilitate refilling the dispenser with rolls 146, 148 and 150 of bandage strips similar to rolls 46, 48, and 50 shown in FIGS. 1-3. The diverging upper side 130 of lower section 126 is tapered outwardly so that upper section 124 can pivot around an even more substantial angle of rotation when case 122 is opened.

Figure 7:
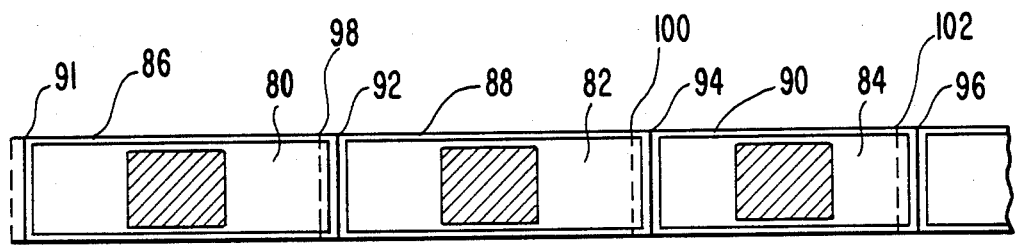
FIG. 7 is a plan view of a section of the packaged roll of bandage strips shown in FIG. 2.
Figure 8:
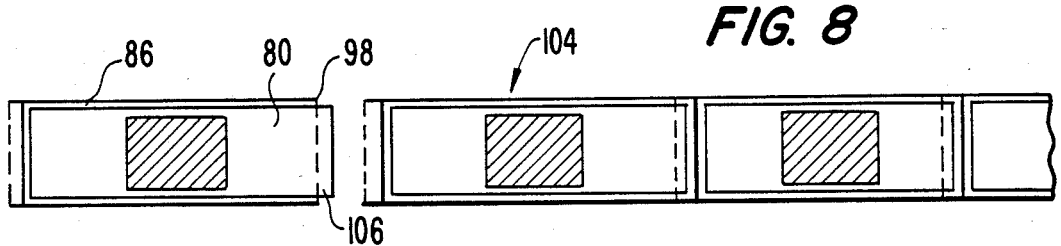
FIG. 8 is a plan view of packaged bandage strips shown in FIG. 7 with the leading strip and packaging material removed from the remainder of the roll.
Figure 9:
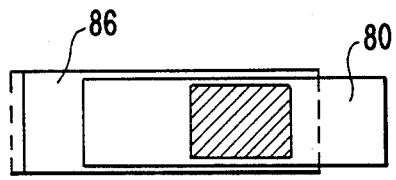
FIG. 9 shows the separated bandage strip of FIG. 8 partially removed from its packaging.

FIGS. 7-9 show a plan view of a portion of the package roll bandage strips as rolls 46, 48 and 50 shown in FIG. 2. Such packaged rolls of bandage strips comprise, in a unique packaging arrangement, a series of conventional bandage strips 80, 82, and 84 such as those with conventional peel away paper covering adhesive end portions and a center gauze section. Bandage strips 80, 82, and 84 are disposed in end-to-end relation. Packaging material 86, 88, and 90, such as a sleeve of paper or plastic material, surround the bandage strips 80, 82, and 84 for maintaining the strips in the end-to-end relationship and in sterile condition.

Transverse seal means such as sealed areas 92, 94, and 96 constitute sealed lines in packaging material 86, 88, and 90 for maintaining the strips 80, 82, and 84 sterilely separate from each other. As shown in FIG. 7, line of weakness means such as lines of weakness 98, 100, and 102 in the packaging material are each located forward of respective seal means 92, 94, and 96 for aiding separation of the packaging material 86 and a corresponding bandage strip 80 from the remainder of the roll 104 while maintaining the bandage strips in the remainder of the roll 104 in a sealed sterile condition as shown in FIG. 8. In such a manner, the packaging material for a bandage strip is opened as the unit is separated from the roll without the need for further effort.

The length of a strip 80 is greater than the distance between the seal means 91 forward of the strip and the line of weakness 98 behind the respective seal means so that strip 80 is easily removed from the package material after separation of the packaging material along the line of weakness 98. As best seen in FIG. 8, end portion 106 of strip 80 extends out of packaging material 86 so that it is easily grasped and removed from packaging material 86 as shown in FIG. 9. For a tidy arrangement, lines of weakness are transverse and at right angles to the longitudinally extent of the roll and are spaced substantially farther away from the transverse seal means forward of its position than the transverse seal means rearward of its position.

To further facilitate the process of identification and selection of the appropriate bandage strip, the case 22 includes means for identifying the bandage strips. For example, an illustration 108, 110, and 112 of a bandage strip proximate to each slot 52, 54, and 56, respectively, can represent the bandage strip in a roll behind each respective slot.

Additional advantages and modifications will readily occur to those skilled in the art. The invention in its broader aspects is, therefore, not limited to the specific details, representative apparatus, and illustrative examples shown and described. Accordingly, departures may be made from such details without departing from the spirit or scope of applicants general inventive concept.

What is claimed is:

1. Packaged rolls of bandage strips comprising:
 a series of bandage strips disposed in end-to-end relation;
 packaging material surrounding the bandage strips for maintaining the strips in the end-to-end relationship and in a sterile condition;
 transverse seal means in the packaging material for maintaining the strips sterilely separate from each other;
 line of weakness means in the packaging material, each located forward of a respective seal means for aiding separation of the packaging material and a corresponding bandage strip from the remainder of the roll while maintaining the bandage strips in the remainder of the roll in a sealed, sterile condition, and
 wherein the length of a strip is greater than the distance between the seal means forward of the strip and the line of weakness means behind the respective seal means so that the strip is easily removable from the packaging material after separation of the packaging material along the line of weakness means.

2. Packaged rolls of bandage strips as claimed in claim 1 wherein the lines of weakness means are transverse and at right angles to the longitudinal extent of the roll.

3. Packaged rolls of bandage strips as claimed in claim 1 wherein a line of weakness means is spaced substantially farther away from the transverse seal means forward of its position than the transverse seal means rearward of its position.

* * * * *